United States Patent [19]

Fischer et al.

[11] Patent Number: 4,804,786

[45] Date of Patent: Feb. 14, 1989

[54] PREPARATION OF 4-MONOACETALS OF 2-METHYLBUT-2-ENE-1,4-DIAL

[75] Inventors: Rolf Fischer, Heidelberg; Bernhard Schulz, Schwetzingen, both of Fed. Rep. of Germany

[73] Assignee: BASF Aktiengesellschaft, Rheinland-Pfalz, Fed. Rep. of Germany

[21] Appl. No.: 3,796

[22] Filed: Jan. 16, 1987

[30] Foreign Application Priority Data

Jan. 25, 1986 [DE] Fed. Rep. of Germany ....... 3602253

[51] Int. Cl.$^4$ .............................................. C07C 43/30
[52] U.S. Cl. ..................... 568/591; 568/590
[58] Field of Search ............... 568/491, 590, 591, 459, 568/460

[56] References Cited

U.S. PATENT DOCUMENTS

| | | | |
|---|---|---|---|
| 2,561,254 | 7/1951 | Whetstone et al. | 568/460 |
| 3,072,727 | 1/1963 | Howard et al. | 568/591 |
| 3,127,450 | 3/1964 | Lorette et al. | 568/591 |
| 3,166,600 | 1/1965 | Lorette et al. | 568/591 |
| 3,978,092 | 8/1976 | Ichikawa et al. | 568/591 |
| 4,256,643 | 3/1981 | Jaedicke et al. | 260/340.7 |
| 4,579,979 | 4/1986 | Andrade et al. | 568/591 |

FOREIGN PATENT DOCUMENTS

| | | |
|---|---|---|
| 0090231 | of 0000 | European Pat. Off. |
| 0009752 | 4/1980 | European Pat. Off. |
| 2365421 | 12/1974 | Fed. Rep. of Germany ...... 568/591 |
| 2357752 | 5/1975 | Fed. Rep. of Germany ...... 568/591 |
| 2357810 | 5/1975 | Fed. Rep. of Germany ...... 568/591 |
| 2513999 | 10/1976 | Fed. Rep. of Germany ...... 568/591 |
| 2225612 | 7/1982 | Fed. Rep. of Germany ...... 568/591 |
| 1422684 | 1/1976 | United Kingdom ............... 568/591 |

*Primary Examiner*—Werren B. Lone
*Attorney, Agent, or Firm*—Oblon, Fisher, Spivak, McClelland & Maier

[57] ABSTRACT

4-Monoacetals of (E)-2-methylbut-2-ene-1,4-dial of the general formula I

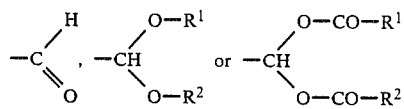

where $R^1$ and $R^2$ are each an aliphatic hydrocarbon radical of 1 to 12 carbon atoms, cycloalkyl of 5 to 7 carbon atoms or benzyl, or $R^1$ and $R^2$ together form an ethylene or propylene radical which may furthermore be substituted by lower alkyl, are prepared by a process in which a compound of the general formula II

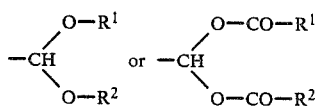

where either $R^3$ and $R^4$ are both one of the groups

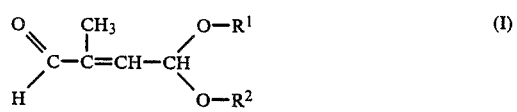

where $R^1$ and $R^2$ have the above meanings, or $R^3$ is one of the groups

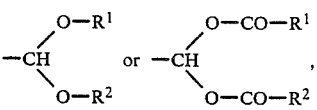

and $R^4$ is formyl

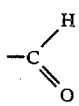

is reacted, at from 20° to 200° C., in the presence of an acidic compound, with the compound of the formula III $$R^5\text{—OH} \qquad \text{(III)}$$

where $R^5$ is hydrogen, alkyl of 1 to 12 carbon atoms or hydroxyalkyl of 2 to 5 carbon atoms, and, where $R^3$ and $R^4$ are each

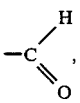

$R^5$ is alkyl, and where $R^3$ and $R^4$ are each

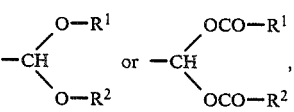

$R^5$ is hydrogen, and where $R^3$ is

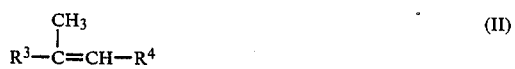

and $R^4$ is

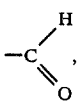

$R^5$ is hydrogen and/or alkyl.

5 Claims, No Drawings

PREPARATION OF 4-MONOACETALS OF 2-METHYLBUT-2-ENE-1,4-DIAL

The present invention relates to a process for the preparation of 4-monoacetals of (E)-2-methylbut-2-ene-1,4-dial (2-methylfumardialdehyde) by reacting 2-methylbut-2-ene-1,4-dial or its 1-monoacetal or 1,4-bisacetal with water and/or an alcohol in the presence of an acidic compound. 4-Monoacetals of (E)-2-methylbut-2-ene-1,4-dial are useful building blocks for the synthesis of various terpenes having biological and pharmacological activity. Several processes for their preparation have been described. For example, German Laid-Open Applications DOS No. 2,357,752 and DOS No. 2,357,810 disclosed that acetals and acylals of 3-methylbut-2-enals can be oxidized with selenium dioxide to 4-acetals of (E)-2-methylbut-2-ene-1,4-dial. According to the process described in German Laid-Open Application DOS No. 2,225,615, cyclic acetals of 3-methylbut-2-en-4-ol-1-al can be oxidised with sulfuric acid/chromic acid solution to give the corresponding 4-acetals of 2-methylbut-2-ene 1,4-dial.

(E)-2-Methylbut-2-ene-1,4-dial 4-acetals can also be prepared according to German Laid-Open Application DOS Nos. 2,513,999 by a multistage process in which, in a first step, a crotonaldehyde acetal is subjected to ozonolysis. European Pat. No. 9,752 describes the reaction of 3-methylbut-3-en-1-al acetals possessing a six-membered ring with nitrosating agents, such as nitrosyl chloride or nitrous acid esters, in the presence of methanol and hydrochloric acid. Hydrogen chloride is eliminated from the resulting 2-chloro-2-methylbutane-1,4-dial bisacetals with a base.

The resulting bisacetals of 2-methylbut-2-ene-1,4-dial, in which a dialkylacetal group is bonded in the 1-position and a cyclic acetal group in the 4-position, can be selectively hydrolyzed to the 4-acetal of 2-methylfumardialdehyde with a dilute aqueous mineral acid.

The prior art processes are not completely satisfactory for the industrial preparation of the desirable 2-methylfumardialdehyde 4-monoacetals, since they are either too complicated or require expensive and/or toxic oxidizing agents, such as selenium dioxide, chromic acid, ozone, nitrosyl chloride or nitrous acid esters.

It is an object of the present invention to provide a process for the preparation of the 4-monoacetals of 2-methylbut-2-ene-1,4-dial starting from readily available starting compounds in a very simple manner, said process being free of the disadvantages of the known processes.

We have found that this object is achieved by a process for the preparation of 4-monoacetals of (E)-2-methylbut-2-ene-1,4-dial of the general formula I $$\underset{H}{\overset{O}{\underset{\|}{C}}}-\underset{\underset{CH_3}{|}}{C}=CH-CH\underset{O-R^2}{\overset{O-R^1}{\diagup}} \qquad (I)$$

where $R^1$ and $R^2$ are each an aliphatic hydrocarbon radical of 1 to 12, preferably 1 to 4, carbon atoms, cycloalkyl of 5 to 7 carbon atoms or benzyl, or $R^1$ and $R^2$ together form an ethylene or propylene radical which may furthermore be substituted by alkyl of 1 to 4 carbon atoms, preferably methyl, wherein a compound of the general formula II $$R^3-\underset{\underset{CH_3}{|}}{C}=CH-R^4 \qquad (II)$$

where either $R^3$ or $R^4$ are both one of the groups $$-C\underset{O}{\overset{H}{\diagup\!\!\!\diagdown}} \; , \; -CH\underset{O-R^2}{\overset{O-R^1}{\diagup}} \; \text{or} \; -CH\underset{O-CO-R^2}{\overset{O-CO-R^1}{\diagup}}$$

where $R^1$ and $R^2$ have the above meanings, or $R^3$ is one of the groups $$-CH\underset{O-R^2}{\overset{O-R^1}{\diagup}} \; \text{or} \; -CH\underset{O-CO-R^2}{\overset{O-CO-R^1}{\diagup}}$$

and $R^4$ is formyl $$-C\underset{O}{\overset{H}{\diagup\!\!\!\diagdown}}$$

is reacted, at from 20° to 200° C., preferably from 40 to 150° C., in the presence of an acidic compound, with a compound of the formula III $$R^5-OH \qquad (III)$$

where $R^5$ is hydrogen, alkyl of 1 to 12, preferably 1 to 4, carbon atoms, in particular methyl, or hydroxyalkyl of 2 to 5 carbon atoms, and where $R^3$ and $R^4$ are each $$-C\underset{O}{\overset{H}{\diagup\!\!\!\diagdown}}$$

$R^5$ is an alkyl, and where $R^3$ and $R^4$ are each $$-CH\underset{O-R^2}{\overset{O-R^1}{\diagup}} \; \text{or} \; -CH\underset{O-CO-R^2}{\overset{O-CO-R^1}{\diagup}} \; ,$$

$R^5$ is hydrogen, and where $R^3$ is $$-CH\underset{O-R^2}{\overset{O-R^1}{\diagup}} \; \text{or} \; -CH\underset{OCO-R^2}{\overset{OCO-R^1}{\diagup}}$$

and $R^4$ is $$-C\underset{O}{\overset{H}{\diagup\!\!\!\diagdown}}$$

$R^5$ is hydrogen and/or an alkyl.

In practice, this means essentially that, in order to prepare 4-monoacetals of (E)-2-methylbut-2-ene-1,4-dial of the general formula I, a 1,4-bisacetal of the formula II is reacted with water in the presence of an acidic compound, 2-methylbut-2-ene-1,4-dial is reacted with an alkanol in the presence of an acidic compound, or 1-monoacetals of (E)-2-methylbut-2-ene-1,4-dial of the general formula II are reacted with water and/or an alkanol in the presence of an acidic compound. In a particularly advantageous process, the 4-monoacetals of (E)-2-methylbut-2-ene-1,4-dial of the general formula I are isolated from the resulting reaction mixture by distillation, the resulting additional mixture of 2-methylbut-2-ene-1,4-dial and its mono- and bisacetals is converted in a conventional manner to bisacetals of the general formula II and the latter are recycled to the reaction according to the invention.

This finding is surprising since it could not be foreseen that the reaction of 1-monoacetals of 2-methylbut-2-ene-1,4-dial with water and alcohols and of 2-methylbut-2-ene-1,4-dial with alcohols would very predominantly give 4-monoacetals of 2-methylbut-2-ene-1,4-dial.

In view of European Pat. No. 9,752 it could not be foreseen that it would be possible to convert bisacetals of 2-methylbut-2-ene-1,4-dial, in which the two acetal groups are identical, virtually selectively to 4-monoacetals of 2-methylbut-2-ene-1,4-dial.

It was also surprising that the isomeric 1-acetals and 4-acetals of 2-methylbut-2-ene-1,4-dial can be separated by distillation.

Examples of suitable starting compounds of the formula II are the 1-mono- and 1,4-bisacetals of 2-methylfumardialdehyde, in the form of the dimethyl, diethyl, di-n-propyl, di-n-butyl, diisobutyl, dicyclohexyl, dicyclopentyl and dibenzyl acetals. Examples of appropriate cyclic acetals are those based on ethylene glycol, propylene glycol or neopentyl glycol as dihydric alcohol components. 2-Methylfumardialdehyde itself is also suitable. It is also possible to use mixtures of the stated compounds which may furthermore contain the corresponding (Z)-isomers of the compounds II.

Examples of suitable 1-mono- and 1,4-bisacylals of 2-methylfumardialdehyde are compounds based on the carboxylic acids of formic acid, acetic acid, propionic acid, butyric acid, cyclohexanecarboxylic acid and phenylacetic acid.

The preparation of (E)-2-methyl-4,4-dimethoxybut-2-enal by reacting 2-methyl-1,1,4,4-tetramethoxybut-2-ene with water in the presence of a strongly acidic ion exchanger can be described, for example, by the following equation:

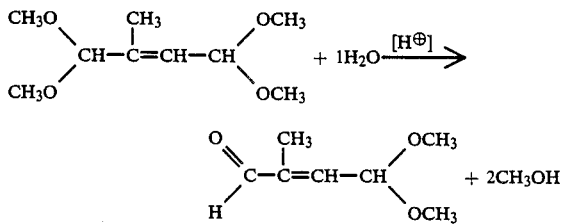

Unconverted starting materials, 3-methyl-4,4-dimethoxybut-2-enal and 2-methylbut-2-ene-1,4-dial occur as byproducts in this procedure. A particular advantage of the process is that first the desired 2-methyl-4,4-dimethoxybut-2-enal can be separated from the stated byproducts by distillation, the resulting mixture of 2-methylbut-2-ene-1,4-dial and its mono- and bisacetals can be converted with an acetalizing agent, such as an alcohol or orthoester, in a conventional manner back into 2-methyl-1,1,4,4-tetramethoxybut-2-ene, and the latter can be reused for the preparation of 2-methyl-4,4-dimethoxybut-2-enal.

The starting compounds of the formula II are obtainable by different methods. For example, 2-methylbut-2-ene-1,4-dial can be prepared by hydrolysis of 2-methyl-4,4-diacetoxybut-2-enal (cf. European Pat. No. 90,231). 3-Methyl-4,4-dimethoxybut-2-enal can be obtained, for example, by oxidizing 3-methyl-4,4-dimethoxybut-2-enol. 2-Methyl-1,1,4,4-tetramethoxybut-2-ene can be prepared by reacting 2-methylbut-2-ene-1,4-dial or 3-methyl-4,4-dimethoxybut-2-enal with methanol or trimethyl o-formate or by thermal decomposition of the bis-dimethylacetal of 1,2-diformylcyclopropane.

Examples of suitable compounds of the formula III are water, methanol, ethanol, n-propanol, isopropanol, n-butanol, 2-ethylhexanol, n-octanol, cyclohexanol, cyclopentanol, benzyl alcohol, ethylene glycol, 1,2- and 1,3-propylene glycol, 2-methyl-1,3-propylene glycol and 2,2-dimethyl-1,3-propylene glycol (neopentylglycol). It is also possible to use mixtures of water and one of the stated alcohols.

The molar ratio of starting compound II to compound III is 1:20, in particular 1:5.

The acidic agents used are, for example, aliphatic carboxylic acids, such as formic acid, acetic acid, propionic acids or valeric acids, sulfonic acids, such as p-toluenesulfonic acid, or mineral acids, such as hydrochloric acid, sulfuric acid or hydrobromic acid. It is also possible to use cation exchangers in their acidic form, for example exchangers which are composed of styrene and divinylbenzene and contain sulfo groups, or inorganic cation exchangers, such as zeolites, or phenol- or polystyrenesulfonic acid resins, styrenephosphonic acid resins, styrenephosphinic acid resins, or exchangers containing appropriate acidic resins, eg. bifunctional condensation resins.

Examples of cation exchangers of the stated type are the products available commercially under the names Lewatit® S 100, Amberlit® IR-200, Lewasorb®, Dowex® 50 WX 8 and Amberlyst® 15. Other acidic compounds which may be used are Lewis acids, such as boron trifluoride, zinc chloride, iron(III) chloride, aluminum chloride or tin(IV) chloride.

The carboxylic acids of the stated type are used, for example, in amounts of from 0.01 to 1 mole per mole of starting materials II. When the sulfonic acids or the strong mineral acids or Lewis acids are used, catalytic amounts, such as from 0.002 to 0.25 equivalents of the acid per mole of compound II, are sufficient. The amount of cation exchanger depends on the selectivity and on the number of exchangeable groups of the exchanger used, at the reaction temperature. In general, the exchanger is used in an amount of from 1 to 40, preferably from 1 to 25, % by weight, based on starting materials II.

The reaction can be carried out at from 20° to 200° C., in particular from 40° to 150° C., under atmospheric or superatmospheric pressure, batchwise or continuously.

The acetalization of mono- or dialdehydes can be carried out by a conventional method, for example by reaction with an alcohol or orthoester (cf. Houben-Weyl, Methoden der organischen Chemie, 4th edition, Volume 6/3, pages 221–229).

The novel process can be carried out, for example, by heating the starting compound II, for example a bisacetal of 2-methylbut-2-ene-1,4-dial, with the particular amount of water and, for example, a strongly acidic ion exchanger as the acidic compound to the desired temperature. It is also possible to distill off the resulting alcohol during the reaction. After the reaction, the reaction mixture is cooled, the ion exchanger is filtered off and the desired 4-monoacetal of 2-methylbut-2-ene-1,4-dial is isolated by fractional distillation. The mixture of 2-methylbut-2-ene-1,4-dial, monoaldehyde and bisacetal also obtained is converted back to the particular bisacetal by reaction with an acetalizing agent, and the said bisacetal is reused for the novel reaction.

It is also possible to carry out the reaction in the presence of a solvent which is inert under the reaction conditions, eg. a hydrocarbon, chlorohydrocarbon or aromatic hydrocarbon.

The 4-acetals of 2-methylbut-2-ene-1,4-dial are useful intermediates which are used, for example, for the synthesis of terpenes (cf. German Laid-Open Application DOS No. 2,357,810). With the aid of the novel process, they can be prepared in a very simple manner and without the use of expensive and/or toxic oxidizing agents.

EXAMPLE 1

A suspension of 1 g of Amberlite IR 120 (H form) in 47.6 g of (E)-2-methyl-1,1,4,4-tetramethoxybut-2-ene (1) and 5 g of water was heated to 60° C. and stirred at this temperature for 0.5 hour (h). After the mixture had been cooled to room temperature (RT) and the ion exchanger filtered off, the reacted mixture contained, according to quantitative gas chromatographic analysis, 7.6 g of starting material, 22.8 g of 2-methyl-4,4-dimethoxybut-2-enal (2), 5.5 g of 3-methyl-4,4-dimethoxybut-2-enal (3), 1.5 g of 2-methylbut-2-ene-1,4-dial (4) and 0.5 g of 3-methyl-2,5-dimethoxy-2,5-dihydrofuran (5). The ratio of 2-methyl- to 3-methyl-4,4-dimethoxybut-2-enal was thus 81:19.

To isolate 2-methyl-4,4-dimethoxybut-2-enal, the reacted mixture was distilled over a 1 m spinning band column. The composition of the 7 fractions obtained is shown in Table 1 below.

TABLE 1

| Fraction | Amount [g] | Boiling point [°C./18 mbar] | GC analysis (% by area) | | | | |
|---|---|---|---|---|---|---|---|
| | | | (1) | (2) | (3) | (4) | (5) |
| 1 | 1.5 | 47–75 | — | 6.7 | — | 47.6 | 45.0 |
| 2 | 1.4 | 75–77 | — | 55.7 | — | 28.1 | 15.8 |
| 3 | 8.9 | 77–80 | — | 95.6 | — | 2.7 | 1.7 |
| 4 | 11.4 | 80–81 | — | 99.0 | — | 0.1 | 0.2 |
| 5 | 0.8 | 81–86 | 1.0 | 88.3 | 6.1 | | |
| 6 | 5.8 | 86–92 | 6.3 | 9.3 | 80.7 | | |
| 7 | 6.0 | 92–95 | 54.4 | 0.3 | 39.2 | | |

The distillation residue was 0.5 g, and 16.3 g of methanol were present in the cold trap. The yield of (E)-2-methyl-4,4-dimethoxybut-2-enal was 20.5 g (57%), based on (1) employed, assuming that % by area equals % by weight.

Fractions 1, 2, 6 and 7 were combined (14.7 g), 21.2 g of trimethyl o-formate and 0.5 g of Amberlite IR-120 were added and the mixture was stirred for 20 h at RT. Low boilers were stripped off in a rotary evaporator, after which 14.4 g of ((E)-2-methyl-1,1,4,4-tetramethoxybut-2-ene were recovered by distillation.

The selectivity in the preparation of (E)-2-methyl-4,4-dimethoxybut-2-enal was accordingly 82%.

EXAMPLE 2

A solution of 0.9 g of water in 36 g of E-3-methyl-4,4-dimethoxybut-2-enal and 16 g of methanol, in which 1 g of Amberlite IR-120 was suspended, was heated to 60° C. and stirred at this temperature of 0.5 h. After the mixture had been cooled to RT and the ion exchanger filtered off, the reacted mixture contained, according to quantitative gas chromatographic analysis, 1.9 g of 2-methyl-1,1,4,4-tetramethoxybut-2-ene (1), 21.8 g of 2-methyl-4,4-dimethoxybut-2-enal (2), 5.3 of starting material (3), 7.0 g of 2-methylbut-2-ene-1,4-dial (4) and 0.4 g of 3-methyl-2,5-dimethoxy-2,5-dihydrofuran (5). The ratio of 2-methyl- to 3-methyl-4,4-dimethoxybut-2-enal was accordingly 80:20.

As described in Example 1, the reacted mixture was distilled over a spinning band column. The composition of the resulting fractions is shown in Table 2 below.

TABLE 2

| Fraction | Amount [g] | Boiling point [°C./18 mbar] | GC analysis (% by area) | | | | |
|---|---|---|---|---|---|---|---|
| | | | (1) | (2) | (3) | (4) | (5) |
| 1 | 2.5 | 35–76 | — | 22.9 | — | 48.3 | 28.2 |
| 2 | 21.3 | 76–80 | — | 91.0 | 1.7 | 3.1 | 1.5 |
| 3 | 11.0 | 80–90 | 18.9 | 10.4 | 68.3 | | |

The yield of (E)-2-methyl-4,4-dimethoxybut-2-enal was 20.5 g (57%, based on (3) employed). The distillation residue weighed 1.5 g, and 19 g of methanol were present in the cold trap.

EXAMPLE 3

A solution of 1 g of 2-methylbut-2-ene-1,4-dial in 6 g of methanol, in which 0.2 g of the ion exchanger Amberlite IR-120 was suspended, was heated at 55° C. for 5 minutes. After the mixture had been cooled to RT and the ion exchanger filtered off, the reaction mixture was analyzed by gas chromatography. It consisted of 53% of (E)-2-methyl-4,4-dimethoxybut-2-enal, 8% of (E)-3-methyl-4,4-dimethoxybut-2-enal, 10% of 2-methylbut-2-ene1,4-dial and 20% of (E)-2-methyl-1,1,4,4-tetramethoxybut-2-ene.

EXAMPLE 4

A solution of 0.2 g of concentrated sulfuric acid and 1 g of water in 9.5 of 2-methyl-1,1,4,4-tetramethoxybut-2-ene was stirred for 0.5 h at RT. The sulfuric acid was neutralized with solid NaHCO$_3$, after which the mixture was filtered. The filtrate was worked up by distillation in an Allihn apparatus (150° C./20 mbar), 0.8 g of residue and 4.8 g of distillate being obtained. Gas chromatographic analysis gave 55.6% of (E)-2-methyl-4,4-dimethoxybut-2-enal, 2.9% of 2-methylbut-2-ene-1,4-dial, 18.8% of 3-methyl-2,5-dimethoxy-2,5-dihydrofuran and 8.2% of unconverted starting material.

EXAMPLE 5

A solution of 24.5 g of 2-methylbut-2-ene-1,4-dial in 24 g of methanol, in which 1 g of Amberlite IR-120 was suspended, was heated to 60° C. and stirred at this temperature for 0.5 h. The mixture was cooled to RT and the ion exchanger filtered off, after which the reaction mixture was investigated by gas chromatography. Quantitative analysis showed that 41.4% of (E)-2-methyl-4,4-dimethoxybut-2-enal (2), 11.3% of (E)-3-methyl-4,4-dimethoxybut-2-enal (3), 16.8% of starting material (4), 1.4% of 2-methyl-1,1,4,4-tetramethoxybut-2-ene (1)

and 1.6% of 3-methyl-2,5-dimethoxy-2,5-dihydrofuran (5) were present.

As described in Example 1, the reacted mixture was distilled over a spinning band column. The composition of the resulting fractions is shown in Table 3 below.

TABLE 3

| Frac-tion | Amount [g] | Boiling point [°C./18 mbar] | GC analysis (% by area) | | | | |
|---|---|---|---|---|---|---|---|
| | | | (1) | (2) | (3) | (4) | (5) |
| 1 | 7.1 | 67–68 | — | 1.3 | — | 75.7 | 22.3 |
| 2 | 2.2 | 68–75 | — | 17.0 | 0.8 | 73.1 | 5.8 |
| 3 | 17.8 | 75–86 | — | 94.6 | 2.2 | 2.1 | |
| 4 | 5.2 | 86–90 | 4.3 | 11.4 | 81.1 | | |

The yield of (E)-2-methyl-4,4-dimethoxybut-2-enal was 16.8% (47%, based on (4) employed). The distillation residue weighed 1.7 g, and 16.4 g of methanol were present in the cold trap.

EXAMPLE 6

A suspension of 0.1 g of Amberlite IR-120 in 0.6 g of water and 2.1 g of the bisacetal of 2-methylbut-2-ene-1,4-dial and neopentylglycol was stirred for 0.5 h at $100\pm2°$ C. Gas chromatographic analysis of the cooled and filtered reaction mixture showed that it consisted of 20.8% of unconverted bisacetal, 21.4% of the 4-monoacetal, 12.3% of the 1-monoacetal and 31.4% of neopentylglycol. The ratio of 4-monoacetal to 1-monoacetal was accordingly 64:36.

We claim:

1. A process for the preparation of a 4-monoacetal of (E)-2-methylbut-2-ene-1,4-dial of the formula I $$\underset{H}{\overset{O}{\diagdown}}C-\underset{\underset{CH_3}{|}}{C}=CH-CH\underset{O-R^2}{\overset{O-R^1}{\diagup}} \quad (I)$$

where $R^1$ and $R^2$ are each an aliphatic hydrocarbon radical of 1 to 12 carbon atoms, cycloalkyl of 5 to 7 carbon atoms or benzyl, or $R^1$ and $R^2$ together form an ethylene or propylene radical which may furthermore be substituted by alkyl of 1 to 4 carbon atoms, wherein a compound of the formula II $$R^3-\underset{\underset{CH_3}{|}}{C}=CH-R^4 \quad (II)$$

where either $R^3$ and $R^4$ are both one of the groups $$-C\underset{O}{\overset{H}{\diagup}}, \quad -CH\underset{O-R^2}{\overset{O-R^1}{\diagup}} \quad \text{or} \quad -CH\underset{O-CO-R^2}{\overset{O-CO-R^1}{\diagup}}$$

where $R^1$ and $R^2$ have the above meanings, or $R^3$ is one of the groups $$-CH\underset{O-R^2}{\overset{O-R^1}{\diagup}} \quad \text{or} \quad -CH\underset{O-CO-R^2}{\overset{O-CO-R^1}{\diagup}}$$

and $R^4$ is formyl $$-C\underset{O}{\overset{H}{\diagup}}$$

is reacted, at from 20° to 200° C., in the presence of an acidic compound selected from the group consisting of aliphatic carboxylic acids, sulfonic acids, mineral acids and cation exchangers in their acidic form, with a compound of the formula III $$R^5-OH \quad (III)$$

where $R^5$ is hydrogen, alkyl of 1 to 12 carbon atoms or hydroxyalkyl of 2 to 5 carbon atoms, and, where $R^3$ and $R^4$ are each $$-C\underset{O}{\overset{H}{\diagup}},$$

$R^5$ is alkyl, and where $R^3$ and $R^4$ are each $$-CH\underset{O-R^2}{\overset{O-R^1}{\diagup}} \quad \text{or} \quad -CH\underset{O-CO-R^2}{\overset{O-CO-R^1}{\diagup}},$$

$R^5$ is hydrogen, and where $R^3$ is $$-CH\underset{O-R^2}{\overset{O-R^1}{\diagup}} \quad \text{or} \quad -CH\underset{OCO-R^2}{\overset{OCO-R^1}{\diagup}}$$

and $R^4$ is $$-C\underset{O}{\overset{H}{\diagup}}$$

$R^5$ is hydrogen and/or alkyl.

2. A process for the preparation of a 4-monoacetal of (E)-2-methylbut-2-ene-1,4-dial of the formula I as claimed in claim 1, wherein a 1,4-bisacetal of the formula II is reacted with water in the presence of an acidic compound.

3. A process for the preparation of a 4-monoacetal of (E)-2-methylbut-2-ene-1,4-dial of the formula I as claimed in claim 1, wherein 2-methylbut-2-ene-1,4-dial is reacted with an alkanol in the presence of an acidic compound.

4. A process for the preparation of a 4-monoacetal of (E)-2-methylbut-2-ene-1,4-dial of the formula I as claimed in claim 1, wherein a 1-monoacetal of (E)-2-methylbut-2-ene-1,4-dial of the formula I is reacted with water and/or an alkanol in the presence of an acidic compound.

5. A process as claimed in claim 1, wherein the 4-monoacetal of (E)-2-methylbut-2-ene-1,4-dial of the formula I is isolated from the resulting reaction mixture by distillation, the resulting additional mixture of 2-methylbut-2-ene-1,4-dial and its mono- and bisacetals is converted in a conventional manner to a bisacetal of the formula II, and the latter is recycled to the novel reaction.

* * * * *